United States Patent [19]

Rocklage et al.

[11] Patent Number: 4,978,763

[45] Date of Patent: Dec. 18, 1990

[54] NOVEL MANGANESE(II) DTPA CHELATE

[75] Inventors: Scott M. Rocklage, Saratoga; William P. Cacheris, Sunnyvale; Gene Jamieson, Boulder Creek, all of Calif.

[73] Assignee: Salutar, Inc., Sunnyvale, Calif.

[21] Appl. No.: 370,483

[22] Filed: Jun. 23, 1989

Related U.S. Application Data

[63] Continuation of Ser. No. 249,744, Sep. 27, 1988, Pat. No. 4,889,931.

[51] Int. Cl.$^5$ .............................................. C07F 11/00
[52] U.S. Cl. ......................................... 556/50; 556/46
[58] Field of Search .................... 556/50, 49; 540/465; 546/2, 5

[56] References Cited

U.S. PATENT DOCUMENTS

| | | | |
|---|---|---|---|
| 3,131,048 | 4/1964 | Balassa | 556/49 X |
| 3,275,404 | 9/1966 | Firsching | 556/49 X |
| 3,790,610 | 2/1974 | Lum et al. | 556/49 X |
| 4,322,361 | 3/1982 | Wilson et al. | 556/50 |
| 4,647,447 | 3/1987 | Gries et al. | 424/9 |

Primary Examiner—Arthur C. Prescott
Attorney, Agent, or Firm—Lyon & Lyon

[57] ABSTRACT

The process of this invention for preparing Mn(II) chelate comprises forming the Mn(II) chelate by mixing manganese(II) oxide (insoluble) with an aqueous suspension comprising a molar equivalent or molar excess of the insoluble protonated chelating compound at a temperature of from 20° to 50° C. When the reaction is carried out with a protonated chelating agent in the absence of base, a precipitate of the protonated Mn(II) chelate is formed. A low osmolarity Mn(II) chelate solution can be formed from the precipitates by dissolving them in an aqueous solution of base. When the initial chelate forming reaction is carried out in a solution containing a molar equivalent or excess of sodium hydroxide, a low osmolarity solution of the Mn(II) chelate is directly formed with most chelating agents. Preferred chelating compounds for this process include DPDP, DTPA, DCTA, EDTP, DOTA, DOXA, DO3A and EDTA. The Mn(II) chelate precipitates and low osmolarity solutions formed by the above processes are also aspects of this invention.

7 Claims, No Drawings

NOVEL MANGANESE(II) DTPA CHELATE

This application is a continuation of copending application Ser. No. 07/249,744 filed Sept. 27, 1988 now U.S. Pat. No. 4,889,931.

FIELD OF THE INVENTION

This application relates to novel protonated manganese(II) chelate intermediates useful for preparing low osmolarity MRI contrast agent formulations, to the manufacture of low osmolarity MRI contrast agent formulations, and the MRI contrast agent formulation products thereof.

BACKGROUND OF THE INVENTION

Mn(II) chelates are particularly useful as MRI contrast agents because manganese is less toxic than many paramagnetic metal ions, manganese being normally present in the body in low concentrations, and because Mn(II) has optimum properties for enhancing MRI contrast. A number of Mn(II) chelates have been investigated for use as MRI contrast agents and reported in the literature.

Chelates of paramagnetic metal ions are normally formed by reacting an aqueous solution of a paramagnetic metal salt with the chelating agent in approximate molar proportions, yielding an acidic solution of the chelate and salt anion. An alkaline agent such as sodium hydroxide is added to neutralize the solution to a physiologically acceptable pH, introducing further ions (cation). The process yields a hyperosmotic injection solution, increasing the $LD_{50}$ of the drug product. Substantial efforts are then required to separate the chelate from the soluble ions, and lower the toxicity of the final product formulation.

It is an object of this invention to provide an improved process which directly yields either a low osmolarity solution useful as a MRI contrast agent without further purification, or a novel protonated Mn(II) chelate solid which can be easily separated from the reaction mixture and used to prepare a low osmolarity injection solution.

DESCRIPTION OF THE PRIOR ART

U.S. Pat. No. 4,647,447 describes preparation of Mn(II) chelates of diethylenetriaminepentaacetic acid (DPTA), trans-1,2-cyclohexylenediaminetetraacetic acid (DCTA), ethylenediaminetetraacetic acid (EDTA), and a variety of other chelating agents. This patent also discloses the preparation of paramagnetic metal ion chelates of ethylenedinitrilotetrakis(methylphosphonic acid) (EDTP) and 1,4,7,10-tetraazacyclododecanetetraacetic acid (DOTA). The methods described in this patent for preparing Mn(II) chelates comprise the reaction of $MnCO_3$, a water-soluble salt, with the chelate in aqueous solution to yield a chelate solution containing the carbonate ion. Sodium hydroxide is added to raise the pH to 7. The solution is then generally evaporated to dryness. In Example 13, $MnCO_3$ is reacted with ethylenedinitrilotetra(acethydroxamic acid), acetone is added, and after several hours, a precipitated crystallizate of Mn(II) complex is removed, washed and dried at 50° C. in vacuo to yield the dihydrate. In Example 52, $MnCO_3$ is reacted with DTPA, and the solution is heated to 95° C., neutralized with sodium hydroxide solution, filtered and put into ampoules. A lipid conjugate is prepared in Example 57 and purified with a Sephadex G50 column.

Studies of chelating tendencies of metal ions including Mn(II) with N,N'-ethylenebis-(2-(o-hydroxyphenyl))-glycine (EHPG) reported by Frost, A. et al, *J.Am.Chem.Soc.* 80:530 (1958) and with N,N'-di(2-hydroxybenzyl)ethylenediamine-N,N'-diacetic acid (HBED) reported by L'Eplattenier, F. et al, *J.Am.Chem.Soc.* 89:837 (1967) used reagent grade nitrates and chlorides of the metals.

SUMMARY OF THE INVENTION

The process of this invention for preparing Mn(II) chelates comprises forming the Mn(II) chelate by mixing manganese(II) monooxide (MnO) with an aqueous suspension or solution comprising a molar equivalent or molar excess of the chelating compound at a temperature of 20° to 50° C. When the reaction is carried out at a pH of 3 to 5, fully protonated Mn(II) chelate precipitates. A low osmolarity Mn(II) chelate solution can be prepared from the precipitate by dissolving the precipitate in an aqueous solution of 1 to 3 molar equivalents of base. When the initial chelation is carried out in a solution containing a molar equivalent or excess of an inorganic or organic base, a low osmolarity solution of the Mn(II) chelate is directly prepared. Preferred chelating compounds for this process include N,N'-bis-(pyridoxal-5-phosphate)-ethylenediamine-N,N'-diacetic acid or N,N'-bis(3-hydroxy-2-methyl-5-phosphonomethyl-4-pyridylmethyl)ethylenediamine-N,N'-diacetic acid (DPDP), DTPA, DCTA, EDTP, DOTA, EDTA, DOXA AND D03A.

The Mn(II) chelate precipitates and low osmolarity solutions formed by the above processes are also aspects of this invention.

DETAILED DESCRIPTION OF THE INVENTION

The process of this invention yields a protonated Mn(II) chelate precipitate, and in the presence of base, a low osmolarity solution of the Mn(II) chelate suitable for use as a MRI contrast formulation.

The term "substantially protonated" as used herein, is defined to indicate that hydrogen represents at least 75 percent of the cations in the chelate precipitate. Optimally, the chelate precipitates are fully protonated, that is, hydrogen is the exclusive cation (100 percent hydrogen) in the chelate precipitate.

The process yields these products directly, without elaborate and costly purification procedures to remove excess ions. That these results can be achieved by reacting the insoluble manganese(II) monooxide (MnO) with a suspension of insoluble chelating compound (in free acid or fully protonated form) is surprising. Heretofore, it was thought that a soluble form of Mn(II) was required (i.e., a salt) for the chelation, necessitating the introduction of undesired salt anions.

The essential step in the process of the invention is the reaction of MnO, initially in a particulate form, with an aqueous suspension of the chelating compound. The chelating compound is present in equimolar proportions (1:1) or a molar excess of the chelating compound to insure solubilization of all of the MnO, preferably in a fully protonated or free acid form. Preferably, the MnO and chelating compound are reacted in equimolar proportions. The reaction can be carried out at a temperature of from 20° to 50° C., and preferably from 20° to 30° C. The reaction proceeds more rapidly at the elevated temperatures.

In an embodiment of the process for producing a precipitate which can be easily removed from the solution, the reaction is carried out in the absence of base with a suspension of ligand having a pH of less than 3. The reaction yields an acidic solution. A reaction time of from 8 to 10 hours is usually sufficient for completion of the reaction at temperatures above 20° C., and the fully protonated Mn(II) chelate product precipitates immediately. It can be separated from the reaction mixture, washed, dried, and stored for later preparation of the MRI contrast solutions.

The MRI contrast solutions can be formulated from the chelate solid by dissolving the precipitate in an aqueous solution containing 1 to 6 molar equivalents of pharmaceutically acceptable, non-toxic inorganic and/or organic base. Bases having as cations, lithium ion, the sodium ion and especially the calcium ion are suitable. Organic bases can have as cations, ethanolamine, diethanolamine, morpholine, glucamine, N,N-dimethylglucamine, N-methylglucamine, for example. The solution can be formulated at any temperature, but at temperatures of 20° to 40° C., the dissolution occurs at an efficient rate.

In an alternate embodiment of the process suitable with most chelating agents (excluding EDTA) for producing a low osmolarity solution, the reaction is carried out in the presence of 1-6 molar equivalents amount of base. Preferably, the chelating agent is dissolved in the base solution prior to adding the insoluble MnO. A reaction time of from 8 to 10 hours is usually sufficient for completion of the reaction at temperatures above 20° C. This process directly yields a low osmolarity Mn(II) chelate solution suitable for use as an MRI contrast agent after suitable dilution. It can be filtered, sterilized, and distributed to sterile containers immediately.

The method of this invention is suitable for use with any aqueous soluble chelating compound which forms a stable chelate with the Mn(II) ion. One group of suitable compounds is represented by Formula I, the corresponding pharmaceutically acceptable salts thereof, and the phosphate group mono and diesters thereof with mono and polyhydric alkanols having from 1 to 18 carbons, or alkylamino alcohols, each having from 1 to 18 carbons.

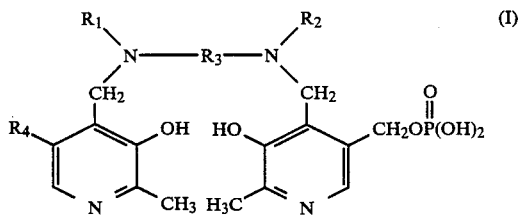

wherein
$R_1$ is hydrogen or

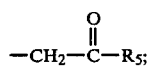

$R_2$ is hydrogen or

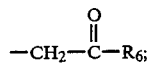

and one of $R_1$ and $R_2$ is other than hydrogen;
$R_3$ is alkylene having from 1 to 8 carbons,
  1,2-cycloalkylene having from 5 to 8 carbons, or
  1,2-arylene having from 6 to 10 carbons, and
$R_4$ is hydrogen, alkyl having from 1 to 6 carbons, or

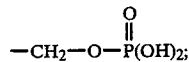

$R_5$ and $R_6$ are each, individually, hydroxy, alkoxy having from 1 to 18 carbons, hydroxy-substituted alkoxy having from 1 to 18 carbons, amino or alkylamido having from 1 to 18 carbons.

The compounds of Formula I and processes for their preparation are described in commonly assigned, copending application Ser. No. 47,614 filed May 8, 1987, which is hereby incorporated by reference in its entirety.

In Formula I, $R_5$ and $R_6$ are preferably each individually hydroxy, alkoxy having from 1 to 8 carbons, ethylene glycol, glycerol, amino or alkylamido having from 1 to 8 carbons. Optimally, $R_5$ and $R_6$ are hydroxy and the salts thereof.

The term "alkyl" and "alkylene", as used herein, include both straight and branch-chained, saturated and unsaturated hydrocarbons. The term "1,2-cycloalkylene" includes both cis and trans cycloalkyl groups and alkyl substituted cycloalkylene groups bonded at the 1,2-positions to respective nitrogen atoms and alkyl substituted derivatives thereof having from 3 to 8 carbons. The term "1,2-arylene" includes phenyl, pyridyl and naphthyl groups bonded at the 1,2-positions to respective nitrogen atoms and alkyl substituted derivatives thereof, having from 3 to 10 carbons.

Since not all of the acidic protons of the chelates are substituted by the central paramagnetic ion, the solubility of the chelate can be increased if a number of the remaining protons are converted to salts of the conjugate base with physiologically biocompatible cations of inorganic and/or organic bases or basic amino acids. For example, the lithium ion, the sodium ion and especially the calcium ion are suitable inorganic cations. Suitable cations of organic bases include, for example, ethanolamine, diethanolamine, morpholine, glucamine, N,N-dimethylglucamine, N-methylglucamine. Lysine, arginine or orithine are suitable cations of basic amino acids, as generally are those of other bases of naturally occurring acids.

The compound, N,N'-bis-(pyridoxal-5-phosphate)ethylene-diamine-N,N'-diacetic acid is referred to hereinafter as DPDP, and the manganese(II) chelate is referred to hereinafter as Mn(DPDP). The compound N-N'-bis(pyridoxal-5-phosphate)-trans-1,2-cyclohexyl-diamine-N,N'-diacetic acid is referred to hereinafter as DPCP, and the manganese(II) chelate is referred to hereinafter as Mn(DPCP).

Other suitable chelating compounds of Formula I include
N,N'-bis(pyridoxal-5-phosphate)-1,3-(n-propylene)-N,N'-diacetic acid,
N,N'-bis(pyridoxal-5-phosphate)-1,2-(n-propylene)-N,N'-diacetic acid, N,N'-bis(pyridoxal-5-phosphate)-1,2-isopropylene-N,N'-diacetic acid,
N,N'-bis(pyridoxal-5-phosphate)-1,2-(n-butylene)-N,N.-diacetic acid,
N,N'-bis(pyridoxal-5-phosphate)-1,3-(n-butylene)-N,N.-diacetic acid,
N,N'-bis(pyridoxal-5-phosphate)-1,2-(3-methylene)propyl-N,N'-diacetic acid,
N,N'-bis(pyridoxal-5-phosphate)-trans-1,2-cyclopentylenediamine-N,N'-diacetic acid,
N,N'-bis(pyridoxal-5-phosphate)-trans-1,2-cycloheptylenediamine-N,N'-diacetic acid,
N,N -bis(pyridoxal-5-phosphate)-trans-1,2-cyclooctylenediamine-N,N'-diacetic acid,
N,N'-bis(pyridoxal-5-phosphate)-1,2-phenylenediamine-N,N'-diacetic acid,
N,N'-bis(pyridoxal-5-phosphate)-cis-1,2-cyclohexylenediamine-N,N'-diacetic acid,
N,N'-bis(pyridoxal-5-phosphate-(N-methylethanolamine)monoester)-ethylenediamine-N,N -diacetic acid,
N,N'-bis(pyridoxal-5-phosphate(N-methylethanolamine)monoester)-1,3-(n-propylene)diamine-N,N'-diacetic acid,
N,N'-bis(pyridoxal-5-phosphate(N-methylethanolamine)monoester)-1,2-(n-propylene)diamine-N,N'-diacetic acid,
N,N'-bis(pyridoxal-5-phosphate(N-methylethanolamine)monoester)-1,2-isopropylenediamine-N,N'-diacetic acid,
N,N'-bis(pyridoxal-5-phosphate(N-methylethanolamine)monoester)-1,2-(n-butylene)diamine-N,N'-diacetic acid,
N,N'-bis(pyridoxal-5-phosphate(N-methylethanolamine)monoester)-1,4-(n-butylene)diamine-N,N'-diacetic acid.
N,N,-bis(pyridoxal-5-phosphate(N-methylethanolamine)monoester)-1,3-(n-butylene)diamine-N,N'-diacetic acid,
N,N'-bis(pyridoxal-5-phosphate(N-methylethanolamine)monoester)-1,2-(3-methyl)propylenediamine-N,N'-diacetic acid,
N,N,-bis(pyridoxal-5-phosphate(N-methylethanolamine)monoester)-trans-1,2-cyclohexylenediamine-N,N'-diacetic acid,
N,N'-bis(pyridoxal-5-phosphate(N-methylethanolamine)monoester)-trans-1,2-cyclopentylenediamine-N,N,-diacetic acid,
N,N'-bis(pyridoxal-5-phosphate(N-methylethanolamine)monoester)-trans-1,2-cycloheptylenediamine-N,N'-diacetic acid,
N,N'-bis(pyridoxal-5-phosphate(N-methylethanolamine)monoester)-trans-1,2-cyclooctylenediamine-N,N'-diacetic acid,
N,N'-bis(pyridoxal-5-phosphate(N-methylethanolamine)monoester)-1,2-phenylenediamine-N,N'-diacetic acid,
N,N'-bis(pyridoxal-5-phosphate(N-methylethanolamine)monoester)-cis-1,2-cyclohexylenediamine-N,N'-diacetic acid,
N,N'-bis-(pyridoxal-5-phosphate)ethylenediamine-N-acetic acid,
N,N'-bis(pyridoxal-5-phosphate)-1,3-(n-propylene)diamine-N-acetic acid,
N,N'-bis(pyridoxal-5-phosphate)-1,2-(n-propylene)diamine-N-acetic acid,
N,N'-bis(pyridoxal-5-phosphate)-1,2-isopropylenediamine-N-acetic acid,
N,N'-bis(pyridoxal-5-phosphate)-1,2-(n-butylene)diamine-N-acetic acid,
N,N'-bis(pyridoxal-5-phosphate)-1,4-(n-butylene)diamine-N-acetic acid,
N,N'-bis(pyridoxal-5-phosphate)-1,3-(n-butylene)diamine-N-acetic acid,
N,N'-bis(pyridoxal-5-phosphate)-1,2-(3-methyl)-propylenediamine- N-acetic acid,
N,N'-bis(pyridoxal-5-phosphate)-trans-1,2-cyclohexylenediamine- N-acetic acid,
N,N'-bis(pyridoxal-5-phosphate)-trans-1,2-cyclopentylenediamine-N-acetic acid,
N,N'-bis(pyridoxal-5-phosphate)-trans-1,2-cycloheptylenediamine-N-acetic acid,
N,N'-bis(pyridoxal-5-phosphate)-trans-1,2-cyclooctylenediamine-N-acetic acid,
N,N'-bis(pyridoxal-5-phosphate)-1,2-phenylenediamine-N-acetic acid,
N,N'-bis(pyridoxal-5-phosphate)-cis-1,2-cyclohexylenediamine-N-acetic acid, and
N,-pyridoxal-N'-(pyridoxal-5-phosphate)ethylenediamine-N,N'-diacetic acid (DPMP).

Another group of suitable compounds are represented by Formula II and the pharmaceutically acceptable salts thereof.

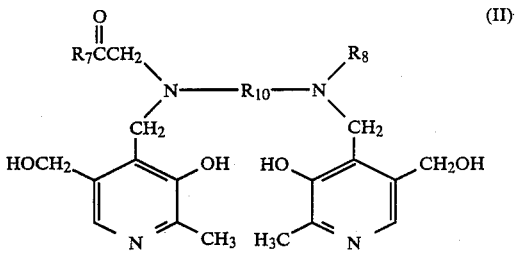

wherein
$R_7$ is hydroxy, alkoxy having from 1 to 18 carbons, hydroxy-substituted alkoxy having from 1 to 18 carbons, amino or alkylamido having from 1 to 18 carbons;
$R_8$ is hydrogen or

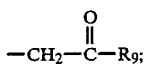

$R_9$ is hydroxy, alkoxy having from I to 18 carbons, hydroxy-substituted alkoxy having from 1 to 18 carbons, amino or alkylamido having from 1 to 18 carbons; and
$R_{10}$ is alkylene having from 1 to 8 carbons, 1,2-cycloalkylene having from 5 to 8 carbons, or 1,2-arylene having from 6 to 10 carbons.

In Formula II, $R_7$ and $R_8$ are preferably each individually hydroxy, ethylene glycol, glycerol, alkoxy having from 1 to 8 carbons, amino or alkylamido having from 1 to 8 carbons. Optimally, R and $R_2$ are each individually hydroxy or the salts thereof.

The compounds of Formula II and processes for their preparation are described in commonly assigned, co-pending application Serial No. 47,584 filed May 8, 1987, which is hereby incorporated by reference in its entirety.

A preferred compound of Formula II is N,N'-bis-(pyridoxal)-ethylenediamine-N,N-diacetic acid. Other suitable compounds include N,N'-bis(pyridoxal)-1,3-(n-propylene)-N,N,-diacetic acid,
N,N'-bis(pyridoxal)-1,2-(n-propylene)-N,N'-diacetic acid,
N,N'-bis(pyridoxal)-1,2-isopropylene-N,N'-diacetic acid,
N,N'-bis(pyridoxal)-1,2-(n-butylene)-N,N'-diacetic acid,
N,N'-bis(pyridoxal)-1,4-(n-butylene)-N,N-diacetic acid,
N,N'-bis(pyridoxal)-1,3-(n-butylene)-N,N'-diacetic acid,
N,N'-bis(pyridoxal)-1,2-(3-methylene)propyl-N,N'-diacetic acid,
N,N'-bis-(pyridoxal)-trans-1,2-cyclohexylenediamine-N,N'-diacetic acid, N,N'-bis(pyridoxal)-trans-1,2-cyclopentylenediamine-N,N'-diacetic acid, N,N'-bis(pyridoxal)-trans-1,2-cycloheptylenediamine-N,N'-diacetic acid, N,N'-bis(pyridoxal)-trans-1,2-cyclo-octylenediamine-N,N'-diacetic acid, N,N'-bis(-pyridoxal)-1,2-phenylenediamine-N,N'-diacetic acid, and N,N'-bis(pyridoxal)-cis-1,2-cyclohexylenediamine-N,N'-diacetic acid.

Another group of chelating compounds are those compounds forming stable Mn(II) chelates represented represented by Formula III or

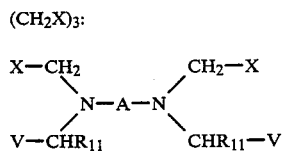

$$\begin{array}{c} X-CH_2 \\ \diagdown \\ N-A-N \\ \diagup \\ V-CHR_{11} \end{array} \begin{array}{c} CH_2-X \\ \diagup \\ \diagdown \\ CHR_{11}-V \end{array} \quad (III)$$

wherein,
X is —COOY, PO$_3$HY or —CONHOY;
Y is a hydrogen atom, a metal ion equivalent and/or a basic biocompatible cation of an inorganic or organic base or basic amino acid;
A is

—CHR$_{12}$—CHR$_{13}$—,

—CH$_2$—CH$_2$(ZCH$_2$—CH$_2$)$_m$, $$\begin{array}{c} N(CH_2X)_2 \\ | \\ -CH_2-CH-CH_2- \end{array}$$

$$\begin{array}{c} CH_2-CH_2-N(CH_2X)_2 \\ | \\ -CH_2-CH_2-N-CH_2-CH_2- \end{array}$$

wherein X is as defined above;
each of R$_{11}$ is hydrogen or methyl;
R$_{12}$ and R$_{13}$ together represent an alkylene group having from 1 to 8 carbons (e.g., trimethylene, tetramethylene, etc.), or individually are hydrogen atoms, lower alkyl groups (e.g., 1-8 carbon atoms), phenyl groups, or benzyl groups;
m represents the number 1, 2 or 3;
Z is an oxygen atom or a sulfur atom or the group $$\diagdown N-CH_2X \text{ or } \diagdown N-CH_2-CH_2-OR_{14},$$

wherein X is as defined above; and

R$_{14}$ is a lower alkyl group (e.g., 1-8 carbon atoms); V has the same meaning as X, or is —CH$_2$OH or —CONH(CH$_2$)$_n$X, wherein X is as defined above;
n is an integer of from 1 to 12;
or if R$_{11}$, R$_{12}$ and R$_{13}$ are hydrogen atoms, both V's together are the group $$\begin{array}{c} CH_2X \\ | \\ -(CH_2)_w-N-CH_2-CH_2-N-(CH_2)_w- \\ | \\ CH_2X \end{array}$$

wherein X is as defined above
w is the number 1, 2 or 3.

Included within the compounds of Formula III are the manganese(II) chelates of diethylenetriaminepentaacetic acid (DTPA) and its analogs.

Other suitable chelating compounds of Formula II are trans-1,2-cyclohexylenediamine-N,N,N',N'-tetraacetic acid, 1,2-ethylenediamine-N,N,N'N'-tetramethanephosphonic acid, 1,4,7,10-tetraazacyclododecane-N,N',N'',N''',-tetraacetic acid, N,N'-bis(1-hydroxybenzyl)ethylenediamine-N,N'-diacetic acid, nitrilo-N,N',N''-triacetic acid,
13,23-dioxo-15,18,21-tris(carboxymethyl)-12,15,18,21,24-pentaazapentatriacontanedioic acid,
3,9-bis(1-carboxyethyl)-6-carboxymethyl-3,6,9-triazundecanedioic acid,
ethylenediamine-N,N,N',N'-tetraacetic acid,
ethylenedinitrilotetra(acetohydroxamic acid),
1,10-diaza-4,7-dithiadecane-1,1,10,10-tetraacetic acid,
1,2-diphenylethylenediaminetetraacetic acid,
N'-(2-hydroxyethyl)ethylenediamine-N,N,N'-triacetic acid,
1,4,8,11-tetraazacyclotetradecane-N,N',N'',N'''-tetraacetic acid,
1,4,7,10-tetraazacyclododecane-N,N',N''-triacetic acid,
diisopropyl iminodiacetic acid,
diethylenetrinitrilopenta(methylphosphonic acid) and,
1-phenylenthylenediaminetetracetic acid.

The compounds of Formula III and processes for their preparation are described in U.S. Pat. No. 4,647,447, hereby incorporated by reference in its entirety.

A further group of suitable chelating compounds are represented by Formula IV.

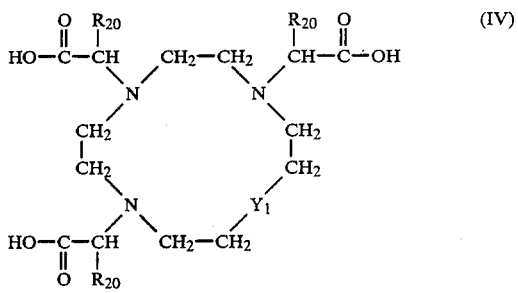

wherein,
Y$_1$ is oxygen or

$R_{20}$ is hydrogen, alkyl, arylalkyl or aryl; and
$R_{21}$ is hydrogen, alkyl, hydroxylalkyl or carboxyalkyl.

Included in the managanese (II) compounds of Formula IV are the manganese (II) chelates of DOTA wherein $R_{20}$ is hydrogen, and $Y_1$ is carboxymethylimino; DO3A wherein $R_{20}$ is hydrogen, and $Y_1$ is alkylimino and preferably methylimino.

Included in the compounds of Formula IV are the manganese(II) chelates of
4,7,10-triscarboxymethyl-1-oxo-4,7,10-triazacyclododecane (DOXA),
1,4,7-triscarboxymethyl-1,4,7,10-tetraazacyclododecane, 1-methyl-4,7,10-triscarboxymethyl-1,4,7,10tetraazacyclododecane, and
1-benzyl-4,7,10-triscarboxymethyl-1,4,7,10-tetraazacyclododecane.

The chelating compounds of Formula IV and methods for their preparation are described in European Patent Application No. 87100635.9, the entire contents of which is hereby incorporated by reference. DOTA and its preparation are described in U.S. Pat. No. 4,647,447.

Optimal chelating compounds include DPDP, EDTP, EDTA, DTPA, DCTA, DOXA, D03A, and DOTA.

The diagnostic media for administration is formulated using physiologically acceptable media in a manner fully within the skill of the art. For example, the chelate salts, optionally with the addition of pharmaceutically acceptable excipients, are suspended or dissolved in an aqueous medium, and then the solution or suspension is sterilized. Suitable additives include, for example, physiologically biocompatible buffers (as, for example, tromethamine hydrochloride), slight additions of other chelating agents (as for example, diethylenetriaminepentacetic acid) or, if necessary, calcium salts (for example, calcium chloride, calcium lactate, calcium gluconate or calcium ascorbate), and calcium chelates.

If suspensions of the chelate salts in water or physiological salt solutions are desired for oral administration, a small amount of soluble chelate salt is mixed with one or more of the inactive ingredients traditionally present in oral solutions and/or surfactants and/or aromatics for flavoring.

The most preferred mode for administering paramagnetic metal chelates as contrast agents for NMRI analysis is by intravenous administration. Intraveneous solutions must be sterile, free from physiologically unacceptable agents, and should be isotonic or iso-osmotic to minimize irritation or other adverse effects upon administration. Suitable vehicles are aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON'S PHARMACEUTICAL SCIENCES. 15th Ed., Easton: Mack Publishing Co. pp 1405-1412 and 1461-1487 (1975) and THE NATIONAL FORMULARY XIV. 14th Ed. Washington: American Pharmaceutical Association (1975), the contents of which are hereby incorporated by reference. The solutions can contain preservatives, antimicrobial agents, buffers and antioxidants conventionally used in parenteral solutions, selecting excipients and other additives which are compatible with the chelates and which will not interfere with the manufacture, storage or use of the products.

The diagnostic media according to this invention can contain from 0.001 to 5.0 moles per liter and preferably from 0.1 to 0.5 moles per liter of the chelate salt.

The chelates of this invention are administered to patients for imaging in amounts which are sufficient to yield the desired contrast. Generally, dosages of from 0.001 to 5.0 mmoles of contrast agent per kilogram of patient body weight are effective to achieve reduction of relaxivity rates. The preferred dosages for most NMRI applications are from 0.05 to 0.5 mmoles of contrast agent per kilogram of patient body weight.

Methods for applying the contrast agents to improve NMRI images, equipment and operating procedures are described by Valk, J. et al, supra. The contrast agents can be used orally and intravenously.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the past tense.

EXAMPLE 1

MnDPDP Precipitate $H_8DPDP.2H_{20}$ (1.00 gm, 1.48 mmoles) and MnO (0.104 gm, 1.46 mmoles) were slurried in 10 mL of water containing ascorbic acid (0.002 gm, 0.01 mmoles) in a 20 mL Erlenmeyer flask. The head space was purged with nitrogen, and the flask sealed with a rubber septum. Within 2 hr, the solution turned yellow, and no MnO particles were observed. The reaction was allowed to stir overnight. The yellow product was isolated by filtration and dried to a constant weight. A quantitative yield of product was obtained. (MnDPDP, m.w. 691 gm/mole)

The characterization follows:

Thermal Gravimetric Analysis (TGA): (30°-270° C., 10°/min, $N_2$).

Calculation for trihydrate: 7.2%; found 8.2% (average of two runs).

Analysis calculated and (found) for
$C_{22}H_{30}MnN_4O_{14}P_2.3H_2O$: C, 35.44 (35.08); H, 4.83; (5.03); N, 7.52 (7.40); Mn, 7.37 (7.36).

Negative ion liquid secondary ion mass spectrometry (n-LSIMS) calculated for $[M-1]^-$ peak and (found): m/z 690 (690).

EXAMPLE 2

MnEDTP Precipitate $H_8EDTP$ (1.165 gm, 2.50 mmoles) and MnO (0.176 gm, 2.50 mmoles) were slurried in 10 mL of distilled water. The suspension was stirred and turned white after four hours. Solid $H_6MnEDTP$ (mw TM 489.05 gm/mole) was isolated by filtration and washed with water and methanol before drying at 50° C. A quantitative yield of product was obtained.

The characterization follows: Negative ion liquid secondary ion mass spectrometry (n-LSIMS)

calculated and (found) for [M-1]$^-$ peak: m/z 488 (488). Osmolality at pH 6.5 (normalized to 1 M): 3.26 Osmoles/Kg.

EXAMPLE 3

MnEDTA Precipitate

H$_4$EDTA (0.730 gm, 2.50 mmoles) and MnO (0.176 gm, 2.49 mmoles) were slurried in 10 mL of distilled water. The suspension was stirred and turned red in color after four hours. After stirring for an additional eight hours, the suspension had a slight pink color which turned to a completely white suspension upon heating at 45° C. for ten min. Solid H$_2$MnEDTA (mw =345.17 gm/mole) was isolated by filtration and washed with water and methanol before drying at 50° C. A 50% yield of product was obtained. The characterization follows:

Negative ion liquid secondary ion mass spectrometry (n-LSIMS)

calculated and (found) for [M-1]$^-$ peak: m/z 344 (344).

Osmolality at pH 6.5 (normalized to 1 M): 2.54 Osmoles/Kg.

EXAMPLE 4

MnDTPA Precipitate

H$_5$DTPA (0.983 gm, 2.50 mmoles) and MnO (0.177 gm, 2.50 mmoles) were slurried in 10 mL of distilled water. The suspension was stirred and turned green in color after four hours. After stirring for an additional eight hours, the suspension turned white. Solid H$_3$MnDTPA (mw =446.28 gm/mole) was isolated by filtration and washed with water and methanol before drying at 50° C. A 50% yield of product was obtained.

The characterization follows:

Negative ion liquid secondary ion mass spectrometry (n-LSIMS) calculated and (found) for [M-1]$^-$ peak: m/z 445 (445).

Osmolality at pH 6.5 (normalized to 1 M): 2.98 Osmoles/Kg.

EXAMPLE 5

MnDCTA Precipitate

H$_4$DCTA (0.911 gm, 2.50 mmoles) and MnO (0.176 gm, 2.48 mmoles) were slurried in 10 mL of distilled water. The suspension was stirred and turned red in color after four hours. After stirring for an additional eight hours, the suspension had a slight pink color which turned to a completely white suspension upon heating at 45° C. for ten min. Solid H$_2$MnDCTA (mw =399.26 gm/mole) was isolated by filtration and washed with water and methanol before drying at 50° C. A 25% yield of product was obtained.

The characterization follows:

Negative ion liquid secondary ion mass spectrometry (n-LSIMS) calculated and (found) for [M-1]$^-$ peak: m/z 398 (398).

Osmolality at pH 6.5 (normalized to 1 M): 2.56 Osmoles/Kg.

EXAMPLE 6

Low Osmolarity Solution of MnDCTA

H$_4$DCTA.H$_2$O (18.2 gm. 50.0 mmoles) was slurried in H$_2$O (50 mL) and solid NaOH (4.0 gm, 100 mmoles) was added with stirring. The green, insoluble MnO was added, and the slurry was slowly heated to 45° C. for 30 min. The resultant clear solution of MnNa$_2$DCTA was filtered through a 0.22 micron sterile filter into a septum vial which was sealed immediately.

The characterization follows:

Relaxivity: R$_1$ (relaxation rate for T$_1$) 3.60 (mM sec)$^{-1}$

R$_1$ for MnCl$_2$-derived MnDCTA 3.69 (mM sec)$^{-1}$.

Acute Toxicity:

For MnO-derived MnDCTA: LD$_{50}$ (iv, Swiss-Webster mice), 5.4 mmole/Kg; For MnCl$_2$-derived MnDCTA: LD$_{50}$ (iv, Swiss-Webster mice), 4.9 mmole/Kg.

EXAMPLE 7

Low Osmolarity Solution of MnDPDP

H$_8$DPDP 2H$_2$O (9.76 gm, 14.47 mmole) was slurried in H$_2$O (20 mL) and solid NaOH (1.74 gm, 43.4 mmole, 3.0 mole equivalents) was added with stirring. The clear, pale yellow solution was purged for 10 min with nitrogen. The green, insoluble MnO was added, and the slurry was stirred vigorously. After two hr, the homogeneous yellow-orange solution was diluted volumetrically to 50 mL yielding a 289.3 mM solution. The MnDPDPNa$_3$ solution was filtered through a 0.22 micron sterile filter into a septum vial which was sealed immediately.

The characterization follows:

Osmolarity: 960 mOsm/Kg @289.3 mM =3.3 Osmoles/Kg @ 1 M (theoretical is 4 Osmoles) for the above prepared solution. Osmolarity for solutions prepared from MnCl$_2$ =7.6 Osmoles @1 M (theoretical is 8 Osmoles).

Acute Toxicity:

For MnO-derived MnDPDP: LD$_{50}$ (iv, Swiss-Webster mice), 3.1 mmole/Kg.

For MnCl$_2$-derived MnDPDP: LD$_{50}$ (iv, Swiss-Webster mice), 2.5 mmole/Kg.

EXAMPLE 8

Osmolarity Values

The osmolarity values for 1 M solutions prepared with MnO compared to those prepared with MnCl$_2$ are summarized as follows:

| Compound | Prepared From | | | |
|---|---|---|---|---|
| | MnCl$_2$ | | MnO | |
| | Theory$^a$ | Found | Theory | Found |
| MnDPDPH$_x$Na$_{3-x}$ | 6–8 | 7.6 | 2–4 | 3.3 |
| MnDCTAH$_x$Na$_{2-x}$ | 6–7 | — | 2–3 | 2.6 |
| MnEDTAH$_x$Na$_{2-x}$ | 6–7 | — | 2–3 | 2.5 |
| MnDTPAH$_x$Na$_{3-x}$ | 7–8 | — | 3–7 | 3.0 |
| MnEDTPH$_x$Na$_{6-x}$ | 7–11 | — | 3–7 | 3.3 |

$^a$Actual values depend upon solution pH.

We claim:

1. A process for manufacturing a Mn(II) DTPA chelate comprising reacting substantially protonated, insoluble DTPA with MnO in water to form a substantially protonated Mn(II) chelate precipitate.

2. The process of claim 1 wherein the reaction is carried out at a temperature of from 20° to 50° C, and the MnO is reacted with at least one molar equivalent of the DTPA.

3. The process of claim 1 including the step of dissolving the Mn(II) chelate precipitate in an aqueous solution of base.

4. The process of claim 3 wherein the base is a pharmaceutically acceptable base.

5. A process for manufacturing an aqueous Mn(II) chelate solution comprising reacting soluble DTPA with MnO in water in the presence of a quantity of a pharmaceutically acceptable base which is sufficient to yield a Mn(II) chelate solution.

6. The process of claim 5 wherein the reaction is carried out in water in the presence of from 1 to 6 molar equivalents of base.

7. The process of claim 5 wherein the cation of the pharmaceutically acceptable base is lithium, sodium, potassium, calcium, ethanolamine, diethanolamine, morpholine, glucamine, N,N-dimethylglucamine, N-methylglucamine, lysine, arginine or orithine.

* * * * *